(12) United States Patent
Muramatsu et al.

(10) Patent No.: US 6,593,396 B2
(45) Date of Patent: Jul. 15, 2003

(54) DENTURE ADHESIVE

(75) Inventors: Hiroaki Muramatsu, Konosu (JP); Toshihiro Sekiguchi, Hatogaya (JP)

(73) Assignee: Healthtech Corporation, Tokyo (JP)

( * ) Notice: Subject to any disclaimer, the term of this patent is extended or adjusted under 35 U.S.C. 154(b) by 0 days.

(21) Appl. No.: 09/876,104

(22) Filed: Jun. 8, 2001

(65) Prior Publication Data

US 2002/0013384 A1 Jan. 31, 2002

(30) Foreign Application Priority Data

Jun. 19, 2000 (JP) ........................................ 2000-182862

(51) Int. Cl.$^7$ .................... A61K 6/08; C08K 3/30; A61C 9/00; C08L 5/04
(52) U.S. Cl. ................. 523/120; 523/118; 524/386; 524/423; 524/486; 524/57; 528/501
(58) Field of Search ................................. 523/120, 118; 433/34, 36, 35; 524/423, 57; 528/501

(56) References Cited

U.S. PATENT DOCUMENTS

| | | | | | |
|---|---|---|---|---|---|
| 4,468,484 | A | * | 8/1984 | Pellico | 523/109 |
| 4,664,630 | A | * | 5/1987 | Lokken | |
| 4,695,463 | A | * | 9/1987 | Yang et al. | |
| 5,024,701 | A | * | 6/1991 | Desmarais | 106/35 |
| 5,206,272 | A | * | 4/1993 | Urabe et al. | |
| 5,760,102 | A | * | 6/1998 | Hall et al. | |

* cited by examiner

Primary Examiner—Tae H. Yoon
(74) Attorney, Agent, or Firm—Oblon, Spivak, McClelland, Maier & Neustadt, P.C.

(57) ABSTRACT

There is provided an adhesion type denture adhesive having superior cleanability, which can be easily removed from a denture base and an oral mucosa for cleansing after the use, while possessing a superior force for stabilizing a denture. The denture adhesive containing a water-soluble polymer as a main ingredient, and containing 0.5 to 60% by weight of an alginate and 0.1 to 20% by weight of calcium sulfate contained therein.

14 Claims, No Drawings

DENTURE ADHESIVE

BACKGROUND OF THE INVENTION

1. Field of the Invention

The present invention relates to an adhesion type denture adhesive having superior cleanability, which can be easily removed from an oral mucosa and a denture base for cleansing after the use.

2. Description of the Conventional Art

A denture adhesive is a material for making unfitted denture stable in a mouth and exhibits an effect for compensating occlusion or mastication to make a person easy to talk. Such a denture adhesive is classified in terms of composition into a so-called "close contact type" denture adhesive containing a vinyl acetate resin as a main ingredient and "an adhesion type" denture adhesive containing a water-soluble polymer having high adhesiveness, such as karaya gum and sodium carboxymethyl cellulose, as a main ingredient.

The close contact type denture adhesive is a denture adhesive that removes air between a denture base and an oral mucosa and vacuum adsorbs a denture on the mucosa surface, thereby stabilizing the denture due to its adhesive properties. In general, the close contact type denture adhesive is an elastic rubber-like paste containing a vinyl acetate resin as a main ingredient. Since this close contact type denture adhesive is insoluble in water, it has characteristics that it is possible to take out the denture from the mouth and wash it with water and that it can be used even in the case where a gap between the denture base and the oral mucosa is relatively large. Further, it can be easily separated from the oral mucosa. However, the close contact type denture adhesive has involved defects such that it has irritation on the oral mucosa due to an alcohol present as one ingredient therein and that the denture adhesive is liable to remain on the resin-made denture surface, whereby works for removing the denture adhesive from the denture base for cleansing after the use are very difficult.

On the other hand, the adhesion type denture adhesive is a denture adhesive containing a water-soluble polymer such as karaya gum and sodium carboxymethyl cellulose, as a main ingredient, in which the water-soluble polymer comes into contact with a saliva between the denture base and the oral mucosa and is swollen and dissolved therein, thereby exhibiting adhesiveness and making the denture stick to the oral mucosa for stabilization.

The adhesion type denture adhesive is further classified, depending on the shape, into a powdered form; a paste-like form prepared by mixing the water-soluble polymer powder with a mineral oil such as Vaseline and liquid paraffin, or an anhydrous polyhydric alcohol such as glycerin and polyethylene glycol; and a sheet-like form prepared by once dissolving the water-soluble polymer powder in a solvent and then drying it by lyophilization or the like.

The adhesion type denture adhesive in any form is superior in stabilization effect to the close contact type denture adhesive and has a characteristic such that it is less in a feeling of wrongness because it can be applied uniformly and thinly between the oral mucosa and the denture base. However, the adhesion type denture adhesive has involved defects such that, since the water-soluble polymer that has been swollen and dissolved in moisture is in a paste-like state, works for removing the denture adhesive stuck to the denture base or oral mucosa for cleansing after the use are difficult and that the denture adhesive attached on the denture base or mucosa surface cannot be easily removed.

SUMMARY OF THE PRESENT INVENTION

An object of the present invention is to overcome the above-described defects of the denture adhesive of the conventional art and provide an adhesion type denture adhesive having superior cleanability while keeping a superior denture stabilization effect, which can be easily removed from a denture base and an oral mucosa for cleansing after the use.

We, the present inventors made extensive and intensive investigations in order to achieve the above-described object. As a result, it has been found that when suitable amounts of an alginate and calcium sulfate are mixed into an adhesion type denture adhesive containing a water-soluble polymer as a main ingredient, not only the resulting adhesion type denture adhesive has superior adhesiveness due to swelling and dissolution of the water-soluble polymer upon contact with moisture such a saliva, but also it becomes in a gel-like state due to a fact that a calcium alginate gel formed by the reaction of the alginate and calcium sulfate during the contact with moisture contains a paste of the water-soluble polymer, whereby it can be easily removed, together with the water-soluble polymer, from a denture base or an oral mucosa for cleansing after the use, leading to accomplishment of the invention.

Specifically, the denture adhesive according to the invention is a denture adhesive containing a water-soluble polymer as a main ingredient, and containing 0.5 to 60% by weight of an alginate and 0.1 to 20% by weight of calcium sulfate.

DETAILED DESCRIPTION OF THE PRESENT INVENTION

As the denture adhesive according to the present invention, any conventional denture adhesive that has hitherto been used can be used without particular restrictions so far as it contains a water-soluble polymer as a main ingredient and utilizes adhesiveness by swelling and dissolution of the water-soluble polymer. When suitable amounts of an alginate and calcium sulfate are mixed into this adhesion type denture adhesive, the resulting denture adhesive can be easily removed from a denture base and an oral mucosa for cleansing after the use, and consequently, it possesses superior cleanability.

Examples of the water-soluble polymer that has hitherto been used for the present invention include karaya gum, sodium carboxymethylcellulose, gum arabic, sodium polyacrylate, and a methoxy ethylene-maleic anhydride copolymer. In the invention, two or more of these water-soluble polymers can also be used at the same time.

Examples of the alginate that is used for the denture adhesive according to the present invention include sodium alginate, potassium alginate, ammonium alginate, and magnesium alginate. A suitable amount of the alginate to be mixed is 0.5 to 60% by weight, and preferably 5 to 30% by weight. When the amount of the alginate to be mixed is less than 0.5% by weight, the effect by a calcium alginate gel cannot be provided. On the other hand, when it exceeds 60% by weight, the operability during the use of the denture adhesive is deteriorated.

The higher a molecular weight of the alginate, the higher a gel strength of calcium alginate as formed, and hence, such is more suitable. Since it is difficult to define the molecular weight of the alginate, it is general to define the molecular weight in terms of a viscosity under prescribed conditions. Accordingly, it is preferred that the alginate used in the invention has a viscosity of 50 to 1,000 cP, and preferably 700 to 1,000 cP at 25° C. in terms of 1% by weight aqueous solution.

Calcium sulfate that is used for the denture adhesive according to the invention may be in the form of either a dihydrate or a semi-hydrate. A suitable amount of calcium sulfate to be mixed is 0.1 to 20% by weight, and preferably 0.3 to 8% by weight. When the amount of calcium sulfate to be mixed is less than 0.1% by weight, the effect for gelling the alginate is not provided. On the other hand, when it exceeds 20% by weight, the fluidity of the denture adhesive during the use is deteriorated, so that the denture adhesive cannot be thinly applied in a gap between the denture base and the oral mucosa.

The denture adhesive according to the invention may be in any of a powder form, a paste-like form, or a sheet-like form, like the adhesion type denture adhesive of the conventional art. In the case where the denture adhesive according to the present invention is in a powder form, a water-soluble polymer powder, an alginate powder and a calcium sulfate powder are mixed and then provided. In this case, the denture adhesive powder is sprayed on a denture base that is moistened by water in advance, and an excess of the denture adhesive is shaken off, followed by inserting the denture into a mouth and providing it for the use.

In the case where the denture adhesive according to the present invention is in a paste-like form, the mixture in a powder form is mixed with a mineral oil such as Vaseline and liquid paraffin, or an anhydrous polyhydric alcohol such as glycerin and polyethylene glycol, in an amount of at most 60% by weight, and preferably 15 to 60% by weight, to prepare a paste. In comparison with the powered denture adhesive, the paste-like denture adhesive does not require a denture to be moistened with water in advance and is spread more uniformly and thinly on the denture base surface. Thus, the latter is superior in the operability.

In the case where the denture adhesive according to the invention is in a sheet-like form, the respective components including the water-soluble polymer, the alginate and the calcium sulfate are once mixed in a solvent and then dried by lyophilization or the like, to prepare a sheet. The sheet-like denture adhesive is moistened by water and laminated on the denture base surface to adjust the shape, followed by inserting the denture into a mouth and providing it for the use.

As a matter of course, the denture adhesive according to the present invention can be mixed with other optional components so far as the effects of the invention are not inhibited. Examples of such optional components that can be used in the present invention include a preservative, a pH adjustor, an enzyme, a pigment, and a fragrance or flavor.

The invention will be specifically described with reference to the following Examples, but it should not be construed that the invention is limited thereto. In each of the Examples and Comparative Examples, the alginate was designated with a viscosity at 25° C. in terms of a 1% by weight aqueous solution.

EXAMPLE 1

| | |
|---|---|
| Karaya gum: | 30% by weight |
| Sodium alginate (780 cP): | 15% by weight |
| Calcium sulfate (dihydrate): | 5% by weight |
| Liquid paraffin: | 50% by weight |

The above components were mixed to obtain a paste-like denture adhesive.

EXAMPLE 2

| | |
|---|---|
| Sodium carboxymethyl cellulose: | 40% by weight |
| Potassium alginate (800 cP): | 10% by weight |
| Calcium sulfate (dihydrate): | 3% by weight |
| White Vaseline: | 47% by weight |

The above components were mixed to obtain a paste-like denture adhesive.

EXAMPLE 3

| | |
|---|---|
| Sodium polyacrylate: | 41% by weight |
| Sodium alginate (700 cP): | 4% by weight |
| Calcium sulfate (dihydrate): | 2% by weight |
| Glycerin: | 53% by weight |

The above components were mixed to obtain a paste-like denture adhesive.

EXAMPLE 4

| | |
|---|---|
| Karaya gum: | 20% by weight |
| Potassium alginate (580 cP): | 25% by weight |
| Calcium sulfate (semi-hydrate): | 15% by weight |
| Polyethylene glycol: | 40% by weight |

The above components were mixed to obtain a paste-like denture adhesive.

EXAMPLE 5

| | |
|---|---|
| Sodium polyacrylate: | 70% by weight |
| Sodium alginate (800 cP): | 25% by weight |
| Calcium sulfate (semi-hydrate): | 5% by weight |

The above components were mixed to obtain a powdered denture adhesive.

EXAMPLE 6

| | |
|---|---|
| Sodium polyacrylate: | 60% by weight |
| Magnesium alginate (580 cP): | 30% by weight |
| Calcium sulfate (dihydrate): | 10% by weight |

The above components were mixed to obtain a powdered denture adhesive.

Comparative Example 1

| Karaya gum: | 35% by weight |
|---|---|
| Calcium sulfate (dihydrate): | 15% by weight |
| Polyethylene glycol: | 50% by weight |

The above components were mixed to obtain a paste-like denture adhesive.

Comparative Example 2

| Karaya gum: | 35% by weight |
|---|---|
| Potassium alginate (780 cP): | 25% by weight |
| Polyethylene glycol: | 40% by weight |

The above components were mixed to obtain a paste-like denture adhesive.

Each of the above-described compositions was evaluated with respect to the cleanability and adhesion in the following manners. The results obtained are shown in Table 1.

Measurement of Adhesion

On an acrylic resin plate of φ10 nm×3 mm, were placed 0.2 g of each of the denture adhesives of the Examples and Comparative Examples and 0.1 g of water. Another acrylic resin plate having the same size was put on the denture adhesive so that the denture adhesive was sandwiched by the two acrylic resin plates. After applying a load of 1 kg for 10 seconds, the denture adhesive as forced out was removed out, and the resulting assembly was allowed to stand at a temperature of 37° C. and at a humidity of 100% for 10 minutes. Then, a force necessary for peeling apart the acrylic resin plates was measured.

Cleanability

Each of the denture adhesives of the Examples and Comparative Examples was applied on a denture base and inserted into a mouth in a customary manner. Five hours after the insertion, the denture base was taken out from the mouth, and easiness of the removal of each of the denture adhesives from the denture base and mouth was evaluated. The cleansing method and evaluation method were carried out in the following manner. That is, the denture base side was cleansed lightly with running water by a brush for denture cleansing, and the time until the denture adhesive had been removed from the denture base surface was evaluated. In the oral mucosa side, the inside of the mouth was rinsed with water for one minute, and the amount of the denture adhesive remaining on the oral mucosa surface was visually evaluated according to the following criteria.

| | |
|---|---|
| A: | The denture adhesive did not substantially remain. |
| B: | A slight amount of the denture adhesive remains. |
| C: | A considerable amount of the denture adhesive remains attached onto the mucosa surface. |

TABLE 1

| | | Cleanability | |
|---|---|---|---|
| | Adhesion (kgf) | Denture base | Oral mucosa |
| Example 1 | 0.65 | 20 sec. | A |
| Example 2 | 0.62 | 15 sec. | A |
| Example 3 | 0.65 | 15 sec. | A |
| Example 4 | 0.63 | 20 sec. | A |
| Example 5 | 0.60 | 15 sec. | A |
| Example 6 | 0.59 | 15 sec. | A |
| Comparative Example 1 | 0.50 | 1 min. | B |
| Comparative Example 2 | 0.52 | 1 min. | C |

As is clear from the results shown in Table 1, it can be confirmed that the denture adhesive according to the present invention is a denture adhesive that can be easily cleansed after the use, while possessing superior adhesion equal to or more than that of the adhesion type denture adhesives of the conventional art.

In the light of the above, the denture adhesive according to the invention is a denture adhesive prepared by mixing suitable amounts of an alginate and calcium sulfate into an adhesion type denture adhesive containing a water-soluble polymer as a main ingredient, which has a sure force for stabilizing a denture by utilizing superior adhesive properties due to the water-soluble polymer and adhesiveness due to an effect of a calcium alginate gel formed by the reaction of the alginate and calcium sulfate, and has superior cleanability due to an effect of the calcium alginate gel formed by the reaction of the alginate and calcium sulfate. Accordingly, the denture adhesive according to the invention is greatly valuable in contributing to users of a denture, the number of which is recently increasing according to the aging.

While the invention has been described in detail and with reference to specific embodiments thereof, it will be apparent to one skilled in the art that various changes and modifications can be made therein without departing from the spirit and scope thereof.

What is claimed is:

1. A denture adhesive comprising a water-soluble polymer, 0.5 to 30% by weight of an alginate, 15 to 60% by weight of a mineral oil, and 0.1 to 20% by weight of calcium sulfate,
    wherein the water-soluble polymer is present in an amount at least 1.5 times the total amount of alginate and calcium sulfate based on wt. %.

2. The denture adhesive as claimed in claim 1, wherein said water-soluble polymer is selected from the group consisting of karaya gum, sodium carboxymethyl cellulose, gum arabic, sodium polyacrylate, and a methoxy ethylene-maleic anhydride copolymer.

3. The denture adhesive as claimed in claim 1, wherein said alginate is selected from the group consisting of sodium alginate, potassium alginate, ammonium alginate, and magnesium alginate.

4. The denture adhesive as claimed in claim 1, wherein the amount of calcium sulfate is from 0.3 to 8% by weight.

5. A denture adhesive in a powder form, comprising the denture adhesive as claimed in claim 1.

6. The denture adhesive as claimed in claim 1, wherein said mineral oil is selected from the group consisting of petrolatum and liquid paraffin.

7. The denture adhesive as claimed in claim 1, further comprising an anhydrous polyhydric alcohol.

8. The denture adhesive as claimed in claim 7, wherein said anhydrous polyhydric alcohol is selected from the group consisting of glycerin and polyethylene glycol.

9. A denture adhesive in a sheet form, comprising the denture adhesive as claimed in claim 1.

10. A method of preparing a denture adhesive in a sheet form, comprising:

i) mixing the denture adhesive of claim 1 with a solvent; and ii) drying by lyphilization.

11. The denture adhesive as claimed in claim 1, wherein the water-soluble polymer is karaya gum, the alginate is sodium alginate and the denture adhesive further comprises a liquid paraffin.

12. The denture adhesive of claim 11, wherein the karaya gum is present in an amount of 30% by weight, the sodium alginate is present in an amount of 15% by weight, calcium sulfate dihydrate is present in an amount of 5% by weight, and the liquid paraffin is present in an amount of 50% by weight.

13. The denture adhesive as claimed in claim 1, wherein the water-soluble polymer is sodium carboxymethylcellulose, the alginate is potassium alginate and the mineral oil is a petrolatum.

14. The denture adhesive as claimed in claim 1, wherein the water-soluble polymer is sodium polyacrylate, the alginate is sodium alginate and the denture adhesive further comprises glycerin.

* * * * *